United States Statutory Invention Registration [19]

[11] Reg. Number: H428

Gilbert

[43] Published: Feb. 2, 1988

[54] 1,2,4,5-TETRAKIS (DIAZIDOMETHYL) BENZENE ENERGETIC POLYAZIDE

[75] Inventor: Everett E. Gilbert, Morristown, N.J.

[73] Assignee: The United States of America as represented by the Secretary of the Army, Washington, D.C.

[21] Appl. No.: 24,097

[22] Filed: Mar. 2, 1987

[51] Int. Cl.[4] ..... C07C 117/00

[52] U.S. Cl. ..... 260/349; 149/122

*Primary Examiner*—John F. Terapane
*Assistant Examiner*—J. E. Thomas
*Attorney, Agent, or Firm*—Anthony T. Lane; Harold H. Card, Jr.; Edward F. Costigan

[57] ABSTRACT

1,2,4,5-tetrakis (diazidomethyl) benzene and a method of making the same by reacting 1,2,4,5-tetrakis (dibromomethyl) benzene with sodium azide in dimethylformamide for three hours at 70° to 80° C.

4 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

1,2,4,5-TETRAKIS (DIAZIDOMETHYL) BENZENE ENERGETIC POLYAZIDE

FIELD OF USE

This invention relates to 1, 2, 4, 5-tetrakis (diazidomethyl) benzene which is a powerful explosive.

BACKGROUND

Compounds containing the azidomethyl groups on the benzene ring are known. However, a literature search has not revealed the presence of a benzene ring having multiple diazidomethyl groups.

SUMMARY OF INVENTION

It is an object of this invention to provide a solid energetic polyazide which is high in azide nitrogen content (72.7%), a solid melting above 80° C., and inexpensively prepared. The maximum nitrogen content of the product of the art is that disclosed in the Statutory Invention Registration H138 (issued Oct. 7, 1986) which was 62%.

PREFERRED EMBODIMENT

The starting compound, 1, 2, 4, 5-tetrakis (dibromomethyl) benzene was prepared by the photochemical bromination of the corresponding tetrakis (bromomethyl) benzene by the procedure of Kerfanto and Soyer, Compt. Rend. Series C, 264, 1072 (1967). Tetrakis (bromomethyl) benzene is commercial available from the Aldrich Chemical Company, Milwaukee, Wis.

1, 2, 4, 5-tetrakis (dibromomethyl) benzene (1.0 g–1.3 mmole), ground sodium azide (1.0 g–15.3 mmole), and N,N-dimethylformamide (15 ml) were mixed and stirred magnetically in a test tube for 3 hours in a 70°–80° C. water bath.

The mixture was poured into water, 6 drops of 15% hydrochloric acid were added, and the mixture was allowed to stand for 3 hours for complete separation of the suspended solid. It was filtered and washed with water. The filter paper with product was removed from the filter, dried to constant weight, and the dry product was then easily removed.

The crude yield varied from 83% to 95% in multiple check runs. The melting point (ex methanol) was 106°–8° C., and it decomposed with gas evolution at that temperature.

The product 1, 2, 4, 5-tetrakis (diazidomethyl) benzene, was tested and found to give the following data for its structure, viz. IR(KBr): 2100 (asym. azide) (S), 1370 (m), 1330 (m), 1240 (sym. azide) (S), 1180 (S), 945 (S), 830 (S), 740 (S), 550 (W), 400 (W) $cm^{-1}$. The structure of I was also established by NMR as follows: $^1H$ NMR (acetone $d_6$): δ8.03 (S,2, ArH), δ6.87 (S, 4, ArCH); $^{13}C$ NMR (acetone $d_6$): δ135.4 (ArC), 127.25 (ArCH), 75.3 (—CH).

PERFORMANCE TESTS

The product was easily detonated by a hammer blow on a hard surface, or by scraping with a spatula. It also exploded upon addition to 80% sulfuric acid at 90° C. However, slow heating in a melting point apparatus showed melting at 106°–8° C. with gas evolution, and continued heating to 180° C. gave further gas evolution and color formation, but without detonation. Detonation did occur upon rapid heating on a spatula over a low flame. No visual change was noted upon heating for 5 hours at 95°.

In comparison with materials which contain only primary azide groups, the product of the present invention is less stable and more sensitive. The material with only primary azide groups was less easily detonated by impact with a hammer, and not easily detonated by scraping with a spatula. It could be decomposed by 80% sulfuric acid at 90 C. without explosion. The product of the art, i.e. hexakis-azidomethyl benzene had a high melting point (162°–5°), and like the product of this invention decomposed with gas evolution at the melting point. Both products exploded upon rapid heating.

What is claimed is:

1. 1, 2, 4, 5-tetrakis (diazidomethyl) benzene.

2. A method of preparing 1, 2, 4, 5-tetrakis (diazidomethyl) benzene comprising mixing, in ratio, about 1.0 g of 1, 2, 4, 5-tetrakis (dibromomethyl) benzene with about 1.0 g of sodium azide in about 15 ml. of dimethylformamide for about three hours at 70° to 80° C.

3. The method of claim 2 additionally comprising, in sequence, pouring the resultant mixture into several volumes of water, adding 15 percent hydrochloric acid to said water, and allowing the aqueous mixture to stand for about three hours for the separation of solids.

4. The method of claim 3 additionally comprising, in sequence, filtering solids out of said aqueous mixture, washing said solids, and drying to constant weight.

* * * * *